United States Patent
Heumann et al.

(10) Patent No.: US 8,131,341 B2
(45) Date of Patent: Mar. 6, 2012

(54) METHOD AND DEVICE FOR POSITIONING A PATIENT SUPPORT IN A MAGNETIC RESONANCE APPARATUS

(75) Inventors: Thomas Heumann, Effeltrich (DE); Hendrik Jeschke, Marloffstein (DE); Stefan Schor, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1061 days.

(21) Appl. No.: 11/947,994

(22) Filed: Nov. 30, 2007

(65) Prior Publication Data

US 2008/0132779 A1 Jun. 5, 2008

(30) Foreign Application Priority Data

Dec. 1, 2006 (DE) .......................... 10 2006 056 885

(51) Int. Cl.
*A61B 5/05* (2006.01)
(52) U.S. Cl. ............ 600/415; 600/410; 600/417; 5/600; 5/601
(58) Field of Classification Search .................. 600/410, 600/415–417; 5/600–601; 324/318, 322
See application file for complete search history.

(56) References Cited

U.S. PATENT DOCUMENTS

| 5,551,430 A | 9/1996 | Blakely et al. |
| 5,928,148 A * | 7/1999 | Wang et al. .................... 600/420 |
| 6,882,877 B2 * | 4/2005 | Bonutti ......................... 600/410 |
| 7,180,294 B2 | 2/2007 | Kohlmüller |
| 7,598,737 B2 * | 10/2009 | Campagna ..................... 324/307 |

FOREIGN PATENT DOCUMENTS

DE   103 35 037 A1   3/2005

* cited by examiner

*Primary Examiner* — Brian Casler
*Assistant Examiner* — Christopher Cook
(74) *Attorney, Agent, or Firm* — Schiff Hardin LLP

(57) ABSTRACT

In a method and a magnetic resonance system for positioning a patient support device of the magnetic resonance system, wherein the magnetic resonance system also has a coil device and the patient support device that has a mounting for accommodation of the coil device at a predetermined position, a detector unit is provided for detection of information describing the coil device and a control device controls a drive unit of the support device to move the support device to a determined position in the magnetic resonance apparatus using only information detected by the detector unit.

10 Claims, 2 Drawing Sheets

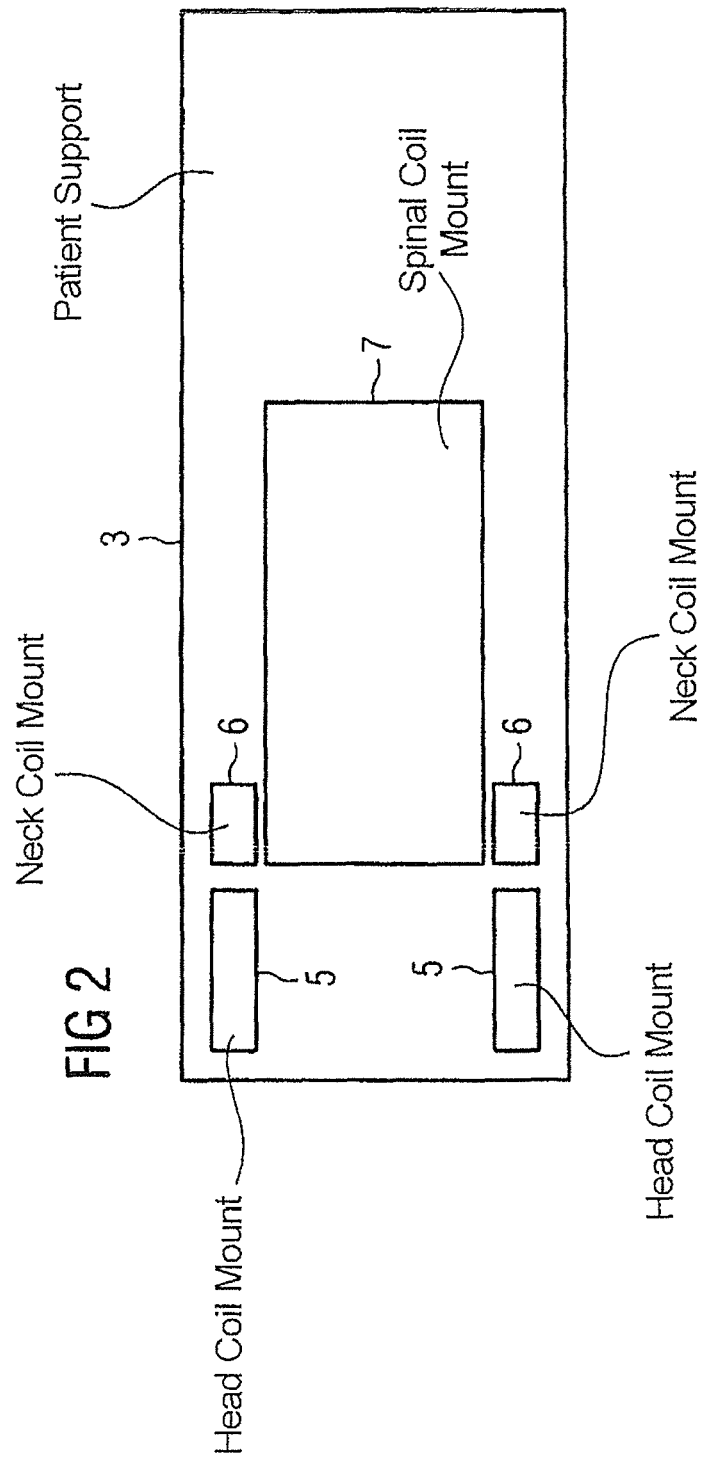

METHOD AND DEVICE FOR POSITIONING A PATIENT SUPPORT IN A MAGNETIC RESONANCE APPARATUS

BACKGROUND OF THE INVENTION

1. Field of the Invention

The present invention concerns a method and a device for positioning a patient support device (patient bed, patient table) in a magnetic resonance apparatus, in particular for positioning such a support device in a magnetic resonance apparatus in combination with one or more local coils of the magnetic resonance apparatus.

2. Description of the Prior Art

In the course of an imaging examination with a magnetic resonance apparatus, the subject to be examined (for example a patient) is first positioned in relation to the measurement center of the magnetic resonance apparatus. In order to avoid unnecessary and costly incorrect measurements, an optimally precise positioning is desirable.

In conventional magnetic resonance apparatuses, the patient is located on a patient bed which can be positioned within the magnetic resonance apparatus using a drive device that is controlled by a control device of the magnetic resonance apparatus. The position of the patient is communicated to the control device of the magnetic resonance apparatus by means of a light marker that is arranged remote and stationary at the magnetic resonance apparatus at a predetermined distance from the magnet center of the magnetic resonance apparatus. Operating personnel manually position the patient bed with the patient located thereon such that the region of the patient to be examined is marked by the light marker. As soon as this manual positioning is concluded, this is communicated to the system by a button press and the patient is automatically positioned in the magnetic resonance apparatus by the control device controlling the drive of the patient bed such that the region to be examined comes to be located in the magnet center.

Antennas known as local or surface coils are frequently used for more precise examination of specific regions (parts) of the patient. For example, these can be special coils for the head, the neck or the spine. These coils are attached on the patient bed and the patient is positioned on the patient bed such that the region of the patient to be examined is aligned to the coils. With the use of the light marker, positioning of the patient bed subsequently ensues in turn relative to the magnet center of the magnetic resonance apparatus. For this purpose, the housings of the local or surface coils have labels (targets) that are aligned on the light marker by operating personnel by manually-controlled movement of the patient bed.

This manually controlled alignment using the light marker requires a not insignificant amount of time. The patient throughput of the magnetic resonance apparatus is thereby reduced, and the work effort for the operating personnel is increased. Both lead to not insignificant costs in the operation of the magnetic resonance apparatus. Moreover, this not insignificant positioning time leads to problems in imaging methods that must be implemented particularly quickly, for example positron emission tomography (PET) examinations, in which the radiation of the substances administered to the patient decreases rapidly, and thus the imaging results become increasingly poorer with advancing time. Moreover, given PET methods the operating personnel should stay in proximity to the patient as briefly as possible in order to receive as low as possible a radiation dose from the patient.

SUMMARY OF THE INVENTION

An object of the present invention is to provide a method and a device that allow positioning of the patient bed of a magnetic resonance apparatus automatically and without manual activation of the patient bed controller by operating personnel. The method should be cost-effective and also easy to retrofit in existing apparatuses.

This object is achieved in accordance with the present invention, by a method for positioning a patient support device of a magnetic resonance apparatus, the magnetic resonance apparatus having a coil device for generation of an alternating magnetic field for nuclear magnetic resonance excitation and/or for reception of the field emanating from the nuclear spins; and a patient support device that supports a subject to be examined (such as, for example, a patient), and a drive unit for moving the support device; and a control device for controlling the drive unit and the coil device. The support device has a mount at a predetermined position for accommodating the coil device. The method includes the steps of initially arranging the coil device in a predetermined mount of the support device, then establishing a communication connection between the coil device and the control device via which coil information is transferred from the coil device to the control device. The coil information describes the type of the coil device, such as, for example, that it is a neck coil, head coil, chest coil or spinal coil. Based only on this coil information, the control device subsequently determines a position of the coil device in the magnetic resonance apparatus and controls the drive unit such that the support device is positioned within the magnetic resonance apparatus according to this predetermined position.

Because the predetermined position of the mount for accommodation of the coil device is used in order to position the support device in the magnetic resonance apparatus, no manual control of the support device by operating personnel is required for alignment with a position designator such as, for example, a light marker. Time and cost for manual positioning of the support device thus can be saved, and additionally the time between a positioning of a patient on the support device and the imaging procedure in the magnetic resonance apparatus can be shortened, so particularly in PET methods better examination results can be achieved.

Moreover, in a treatment by means of HIFU (high-intensity focused ultrasound) in connection with a magnetic resonance apparatus, operating errors can be precluded to a large extent when a special coil with HIFU functionality is used that is likewise arranged at a fixed table position. An incorrect positioning (and thus an incorrectly applied HIFU treatment) is precluded due to the automatic positioning and due to the coil information.

According to a further embodiment, the support device has a number of mounts for accommodation of a number of coil devices. Prioritization information is additionally used to determine the position of the coil devices in the magnetic resonance apparatus. This prioritization information provides a position of the coil devices in the magnetic resonance apparatus for a magnetic resonance measurement (data acquisition) dependent on the combination of the multiple coil devices. It is thus possible to use a number of coils plugged into the system and based on the prioritization, one of these coil devices is used to determine the position of the support device in the magnetic resonance apparatus. The coil information advantageously includes the prioritization information, such that the control device can receive the prioritization information by readout (detection) of the coil information.

According to a further embodiment of the invention, the prioritization information can be set by a user of the magnetic resonance apparatus. It is thereby possible to individually provide each magnetic resonance apparatus with prioritization information according to the desires and interests of the user.

According to a further embodiment of the present invention, the determination of the position of the support device relative to the magnetic resonance apparatus can be augmented by the additional use of the light marker positioning. Via this additional positioning with the aid of a light marker, it is possible to deliberately deviate from the positioning which is predetermined by the coil devices or to use coil devices that provide no coil information, or to operate the magnetic resonance apparatus without additional coil devices, but rather only with a coil permanently installed in the magnetic resonance apparatus.

BRIEF DESCRIPTION OF THE DRAWINGS

FIG. 2 schematically illustrates an inventive support device for the magnetic resonance apparatus shown in FIG. 1.

DESCRIPTION OF THE PREFERRED EMBODIMENTS

Figure 1:
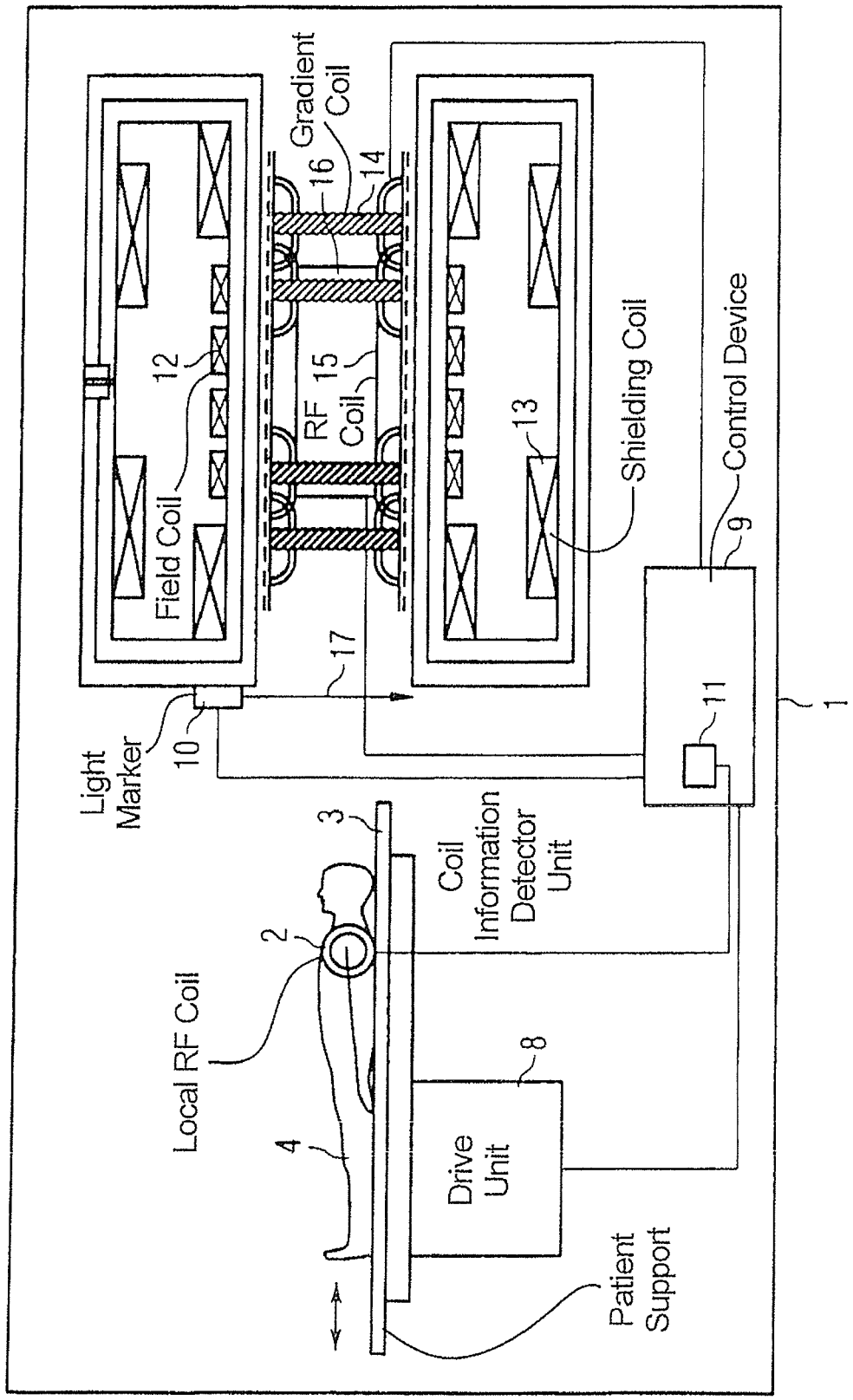
FIG. 1 is a schematic illustration of an inventive magnetic resonance apparatus with a device for positioning a patient support device of the magnetic resonance apparatus.

FIG. 1 is a schematic illustration of an exemplary embodiment of a magnetic resonance apparatus 1. Shielding coils 13 and field coils 12 of the magnetic resonance apparatus 1 generate a temporally constant magnetic field for polarization of the atomic nuclei in the subject 4 to be examined. The field coils 12 and the shielding coils 13 surround a cylindrical hollow space into which the subject 4 to be examined is to be inserted for a magnetic resonance measurement. A cylindrical gradient coil 14 is concentrically inserted into this hollow space and has three sub-windings that generate gradient fields proportional to the respectively applied currents that are spatially perpendicular to one another. Located within the gradient coil 14 is the radio-frequency coil 15, which converts the RF pulses emitted by a power transmitted into an alternating magnetic field for excitation of the atomic nuclei, and subsequently converts the alternating field emanating from the preceding nuclear moment into a voltage fed to a reception branch. Depending on the region of the subject 4, special regionally-sensitive local coils 2 are alternatively used for signal reception. The support device 3 which is driven by a drive unit 8 serves to move the subject 4 to be examined (for example a patient) into the cylindrical hollow space which is defined by the field coils 12 and the shielding coils 13. The control of the gradient coil 14, the radio-frequency coil 15, the local coil 2 and the drive unit 8 of the support device 3 ensues by a control device 9 which (as shown in FIG. 1) is electrically connected with these components. The examination region 16 of the magnetic resonance apparatus is located at approximately a longitudinal center in the axial direction of the cylindrical hollow space which is defined by the field coils 12 and shielding coils 13. An optimally precise positioning of the subject 4 to be examined and the local coil 2 within the measurement center 16 is of decisive importance for the quality of the measurement result.

This positioning can ensue in two ways. Positioning with the aid of a light marker 10 is possible. In this type of positioning, the support device 3 with the subject 4 to be examined and a local coil 2 arranged thereupon is controlled by operating personnel such that the region to be examined is aligned optimally precisely on a light beam 17 of the light marker 10. After this manual alignment by the operating personnel, the conclusion of the alignment is communicated to the control device 9 via a further operating means. The light marker 10 radiates an alignment light ray 17 perpendicular to the longitudinal axis of the cylindrical hollow space which is defined by the field coils 12 and shielding coils 13. Since the light marker 10 is connected in a stationary manner with the magnetic resonance apparatus 1, a fixed distance exists between the marking ray 17 of the light marker 10 and the examination region 16. This distance is known to the control device 9, and thus the subject 4 to be examined together with the local coil 2 and the support device 3 (driven by the drive unit 8) can be positioned precisely in the measurement center 16 by the control device 9.

Alternatively, automatic positioning dependent on the type of the employed local coils 2 is possible as follows. In addition to the actual field coil, a local coil 2 (which is also called a coil device 2 in the following) carries detectable coil information which, for example, identifies the type of the of the coil, i.e. whether it is a head coil, neck coil, spinal coil etc. The coil device also embodies a medium allowing transfer of this coil information to the control device 9 as soon as the coil device 2 is connected with the control device 9. The coil device 2 also has a housing that can be inserted into suitable mounts 5-7 for accommodation of the coil device 2 at the support device 3, as shown in FIG. 2. Positioning of the coil devices 2 in relation to the support device 3 is predetermined by the mounts 5-7 of the support device 3 being designed such that only specific types of coil devices 2 can be inserted into the respective mounting devices 5-7. For example, referring to FIG. 2 the mounts 5 are designed for accommodation of a head coil, the mounts 6 for accommodation of a neck coil and the mount 7 for accommodation of a spinal coil.

When a coil device 2 is suitably inserted into one of the mounts 5-7 and electrically connected with the control device 9, the control device 9 is able to align the support device 2 on the examination region 16 with the aid of a detector unit 11 for readout of the coil information from the coil device 2 so as to detect the type of the coil device 2, such that the corresponding coil device 2 is optimally aligned relative to the examination region 16 for a measurement. The procedure for manual alignment of the support device 3 relative to the light marker thus can be foregone and time and labor can be saved.

If a number of coil devices 2 are simultaneously applied on the support device 3 and these multiple control devices are simultaneously in connection with the control device 9, the coil information also includes prioritization information from which the control device 9 can determine the coil device 2 which is decisive for the positioning of the support device 3.

If the support device 3 is suitable for accommodation of a head coil, a neck coil and a spinal coil, prioritization is possible such that, for example, the neck coil receives the highest priority, the head coil receives the second highest priority and the spinal coil receives the lowest priority. Given the presence of all three coil devices 2, the support device 3 would consequently be optimally positioned with regard to the neck coil. By contrast, given the presence of only the spinal coil and the head coil, the support device 3 would be optimally positioned with regard to the head coil.

Moreover, a programmable prioritization is possible by the priority being stored as part of the coil information in the coil device, for example as a number value, and this number value can be set by a user of the magnetic resonance apparatus. The higher the number value, the higher the priority of the coil device. It is thereby possible to establish a different priority order according to the desires of the user dependent on the main application field of the magnetic resonance system in the respective installation. In the event that a number of coil devices 2 that are simultaneously used in the support device 3 and are connected with the control device 4 exhibit the same highest priority, the support device 3 is, for example, optimally positioned relative to the coil device 2 which is nearest to the measurement center 16 given a backed-out support device. The control device 9 can determine this using previously programmed prior knowledge about the type of the coil device 2 and its general position on the support device 3. In the example shown in FIG. 1 given a completely backed-out support device 3 a head coil would be closer to the measurement center 16 than a neck coil, which would in turn be closer to the measurement center 16 than a back coil.

Although the magnetic resonance apparatus 1 is designed with a mechanism for positioning of the support device 3 using the employed control device 2 as previously described, use of the method described above for positioning the support device 3 with the aid of the light marker 10 is nevertheless available at any time in order to possibly deviate from the optimal positioning for the employed coil device 2.

In addition to the simplified and thus shortened positioning of the subject 4 to be examined in the magnetic resonance apparatus 1 and the therewith shortened positioning time of the patient on the support device and the high patient throughput associated therewith, this type of the positioning in particular offers further advantages given an examination in combination with positron emission tomography. Since the radioactive substance administered to the patient quickly loses radiation intensity, an optimally short preparation time which contains the positioning of the patient in the measurement center is desirable, which can be achieved via the previously presented method. It is also desirable that, in the event of a combined measurement with a positron emission tomography, the operating personnel of the magnetic resonance apparatus reside only as briefly as possible in the area of the patient in order to receive an optimally low radiation dose from the patient. By means of the inventive positioning method that, without manual alignment with the use of a light marker 10, optimally positions the patient 4 in the measurement center 16 given use of coil devices 2, radiation exposure by the operating personnel can be reduced.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for automatically positioning a patient support device of a magnetic resonance apparatus, said magnetic resonance apparatus comprising a plurality of coil devices of different coil types respectively configured to interact with different anatomical regions of a patient, each of said coil devices being operable in at least one of a transmission mode to generate an alternating field for nuclear magnetic resonance excitation of nuclear spins in the patient, and a reception mode to detect a field emanating from the excited nuclear spins, said patient support device comprising a plurality of mounts respectively at different predetermined locations on said patient support device, said plurality of mounts being respectively configured to permit only one of said coil devices of one type to be insertable into each mount, a drive unit that moves the patient support device relative to an examination region of the magnetic resonance apparatus, and a control device that controls the drive unit and the coil devices, said method comprising:

with said plurality of coil devices respectively mounted in said plurality of mounts on said patient support device, establishing a communication link between said plurality of coil devices and said control device;

via said communication link, transferring coil information from said coil devices to said control device, said coil information comprising a designation of at least the type of each of said coil devices;

also providing said control device with prioritization information that designates respective priorities of said coil devices relative to each other for implementing an examination of the patient, including designating one of said plurality of coil devices as having a highest priority;

in said control device, automatically determining respective positions of said plurality of coil devices in said magnetic resonance apparatus using only said coil information, said predetermined positions of said plurality of mounts, and a position of the patient support device relative to a center of said examination region; and from said control device, operating said drive unit to position said patient support device within said magnetic resonance apparatus according to said predetermined positions to cause the coil device with the highest priority to be aligned relative to the center of said examination region.

2. A method as claimed in claim 1 comprising providing said control unit with said prioritization information by manually entering said prioritization information into said control unit.

3. A method as claimed in claim 1 comprising providing said control unit with said prioritization information from said control devices via said communication link, in said coil information.

4. A method as claimed in claim 1 comprising providing, as said plurality of coil devices, a head coil device, a chest coil device, a neck coil device, and a spinal coil device.

5. A method as claimed in claim 1 comprising augmenting positioning of said drive unit according to the positions of the coil devices determined using only said coil information, said predetermined positions of said plurality of mounts, and said position of said patient support device relative to the center of the examination volume, by also using a light marker.

6. A magnetic resonance apparatus comprising:

a patient support device;

a plurality of coil devices of different coil types respectively configured to interact with different anatomical regions of a patient, each of said coil devices being operable in at least one of a transmission mode to generate an alternating field for nuclear magnetic resonance excitation of nuclear spins in the patient, and a reception mode to detect a field emanating from the excited nuclear spins;

said patient support device comprising a plurality of mounts respectively at different predetermined locations on said patient support device, said plurality of mounts being respectively configured to permit only one of said coil devices of one type to be insertable into each mount;

a drive unit that moves the patient support device relative to an examination region of the magnetic resonance apparatus;

a control device that controls the drive unit and the coil devices, said control unit, with said plurality of coil devices respectively mounted in said plurality of mounts on said patient support device, being configured to establish a communication link between said plurality of coil devices and said control device and, via said communication link, to receive coil information from said coil devices, said coil information comprising a designation of at least the type of each of said coil devices;

said control device also being provided with prioritization information that designates respective priorities of said coil devices relative to each other for implementing and examination of the patient, including designating one of said plurality of said coil devices with a highest priority;

said control device being configured to automatically determine respective positions of said plurality of coil devices in said magnetic resonance apparatus using only said coil information, said predetermined positions of said plurality of mounts, and a position of the patient support device relative to a center of said examination region; and said control device being configured to operate said drive unit to position said patient support device within said magnetic resonance apparatus according to said predetermined positions to cause the coil device with the highest priority to be aligned relative to the center of said examination region.

7. An apparatus as claimed in claim 6 wherein said control unit has an interface allowing manual entry of said prioritization information into said control unit.

8. An apparatus as claimed in claim 6 wherein said control unit is provided with said prioritization information from said control devices via said communication link, in said coil information.

9. An apparatus as claimed in claim 6 wherein said plurality of coil devices comprises a head coil device, a chest coil device, a neck coil device, and a spinal coil device.

10. An apparatus as claimed in claim 6 comprising a light marker operable to augment positioning of said drive unit according to the positions of the coil devices determined using only said coil information, said predetermined positions of said plurality of mounts, and said position of said patient support device relative to the center of the examination volume.

* * * * *